United States Patent [19]

Dabi et al.

[11] Patent Number: 4,758,466

[45] Date of Patent: Jul. 19, 1988

[54] FOAM-FIBER COMPOSITE AND PROCESS

[75] Inventors: Shmuel Dabi, Highland Park; Kays B. Chinai, Burlington, both of N.J.

[73] Assignee: Personal Products Company, Milltown, N.J.

[21] Appl. No.: 46,077

[22] Filed: May 5, 1987

[51] Int. Cl.⁴ .................. D04H 1/04; D04H 1/58
[52] U.S. Cl. ............................ 428/283; 264/109; 264/122; 428/288; 428/296; 521/54; 521/178
[58] Field of Search ............ 264/109, 122; 428/283, 428/288, 296; 521/54, 178

[56] References Cited

U.S. PATENT DOCUMENTS

| | | | |
|---|---|---|---|
| 3,900,648 | 8/1975 | Smith | 428/71 |
| 4,105,033 | 8/1978 | Chatterjee | 428/283 |
| 4,110,508 | 8/1978 | Isgur et al. | 428/283 |
| 4,357,386 | 11/1982 | Luciano et al. | 428/283 |
| 4,429,001 | 1/1984 | Kolpin et al. | 428/283 |
| 4,460,642 | 7/1984 | Errede et al. | 428/283 |
| 4,481,248 | 11/1984 | Fraige | 428/283 |
| 4,496,623 | 1/1985 | Fraige | 428/283 |
| 4,554,297 | 11/1985 | Dabi | 521/178 |

*Primary Examiner*—William J. Van Balen

[57] ABSTRACT

A foam-fiber composite, useful as an absorbent for sanitary napkins is disclosed. It is a resilient, absorbent structure made from large particles of an amino-ether hydrophilic foam (and optionally a superabsorbent and wood pulp), which by use of a carding machine is uniformly distributed in, and heat bonded to a fibrous matrix, which matrix is preferably made from two different kinds of fibers, one of which is low melting at the bonding temperatures used in the oven, e.g., polyethylene and the other high melting, e.g., polyester.

25 Claims, No Drawings

FOAM-FIBER COMPOSITE AND PROCESS

This invention relates to a foam-fiber composite which is a resilient, absorbent structure made from a hydrophilic cellular polymer and a thermoplastic fiber, and more particularly to a composite made from large particles of an amino-ether hydrophilic foam uniformly distributed in, and heat bonded to, a fibrous matrix preferably made with both thermoplastic and non-thermoplastic materials, and to the dry process by which it is made.

BACKGROUND OF THE INVENTION

The numerous benefits offered by hydrophilic foam as an alternate absorbing medium for sanitary protection products, e.g., sanitary napkins, has long been recognized. Due to special requirements, this type of foam has to be custom tailored to suit certain applications and, therefore, is scarce. The very few available foams are rather expensive and must be utilized with minimum waste to be economical. One way to accomplish that is molding the product while the foaming takes place. This process is fairly complicated and not always possible. A second way would be to chop or grind the foam into small pieces (large particles) where all of it, including the skin, is fully utilized. As a structure, chopped foam loses its integrity and resiliency, therefore, it has to be rebonded. The latter approach of rebonding is the subject of this invention.

PRIOR ART

U.S. Pat. No. 3,900,648 entitled "Space Filling Material and Method" describes a foam-fiber composite which is a lightweight, space filling material for use as upholstery padding, packing material, thermal insulation, cushion filling, etc. comprising a mass of nonwoven crimped, synthetic filaments and random-shaped cellular foam particles interspersed in said mass, and engaged by and entangled in said filaments. The foam-fiber composite of the patent differs from that of the present invention in the type, size and property requirements of the foam and filaments used, which differ from the amino-ether hydrophilic foams and thermally bondable fibers used to form the composite by thermal bonding, rather than physical entanglement.

U.S. Pat. No. 4,110,508 (W. R. Grace & Co.) describes hydrophilic polyurethane, which is shredded and wet layered to form a sheet. Fibers can be added to that slurry (examples of which are wood fibers which are different than the thermoplastic, thermally fusible fibers required in the present invention). The type of foam and its average particle size is smaller than what is desired in the present invention, and latex binders are added which are not utilized in the instant invention.

SUMMARY OF THE INVENTION

The present invention involves a resilient absorbent material prepared from large particles (small pieces) of an amino-ether hydrophilic foam uniformly distributed in and heat bonded to a thermoplastic fibrous matrix. The preferred matrix is one containing at least two different kinds of fibers in the matrix, one of which is relatively low melting and which has been melted to fuse to some of the foam particles, and the other of which is higher melting and retains its unmelted fiber structure. The composite may additionally also contain other materials, for example, a hydrophilic fiber pulp if desired.

The preferred foam is an amino-ether hydrophilic foam which is the reaction product of amine terminated poly (alkylene oxide) and epoxy resin, and which is disclosed in U.S. Pat. No. 4,554,297 (Personal Products Company), the disclosure of which patent is hereby incorporated herein by reference. Said U.S. Pat. No. 4,554,297 in Examples 1–6 thereof discloses how to make foams, which are there described as products for absorbing body fluids. The foams are useful for the same purpose, when incorporated in the composites of the present invention. That patent also shows how foam samples are tested to determine their various properties, for example, absorbency, resiliency, density, etc. and the test methods shown there are applicable here also for testing the composites of the invention.

DETAILED DESCRIPTION OF THE INVENTION

In the present invention a resilient, absorbent material is prepared from particles of hydrophilic foam, uniformly distributed in a thermoplastic fibrous matrix. If the particle size is too small, particles will fall through the interstices of the fused, fibrous matrix. If the particle size is too large, the composite will not look uniform. We prefer to use a particle size of about 3–8 millimeters (⅛–⅜ inches) but the exact size is not absolutely critical. A more uniform particle size gives a nicer appearance to the final product composite.

The foam, which normally is produced in and exists as large pieces, can be made into the desired particle size either by grinding or chopping it simultaneously with the step of blending it with the fibers, or by pre-grinding it. Where the foam is to be processed simultaneously with the thermoplastic fiber in a carding machine, foam having a tensile strength of about 350 to 4200 Kg/m$^2$ (0.5 to 6 psi) and elongation at break of 5% to 100%, is suitable for use in the current process in the experimental equipment used where the carding and chopping are conducted simultaneously. The preferred foam ranges are about 1050 to 2100 Kg/m$^2$ (1.5–3 psi) tensile strength and 35%–75% elongation at break, to obtain the desired uniformity without stretching the foam significantly. However, where the foam is to be pre-ground or pre-chopped, before the carding operation, even stronger foams may be used if desired. Obviously the particular equipment to be used will influence which strength foams may be used.

The foams which are to be used in the present invention should be heat stable at the temperature that the bonding is to be performed at, and for many uses it would be desirable that the foam not change color at the bonding temperature used. Heat bonding temperatures as high as 155° C., as well as lower temperatures, have been successfully used.

In one embodiment of the process of the present invention, a low density, fluffy uniform blend of foam and fibers was heat bonded to give a resilient structure with good mechanical strength. The foam used was a hydrophilic amino-ether foam made from amine terminated polyoxyethylene and epoxy resin. The fibers used were 3 denier Enka bicomponent polyester-polyethylene. The uniform blend was made by feeding a 3 mm (⅛") sheet of foam, with a layer of fibers on top into a carding machine. The combing action of the carding machine opened the fibers, chopped the foam and randomized the materials, all in one step. The resultant uniform blend was heat treated at 140° C. in an air circulating oven. [This can be done with no pressure beyond atmospheric, or under varying pressure. The specific pressure applied will control the density of the final composite, where a densified composite is desired.] Under these conditions, only the polyethylene outer sheath portion of the bicomponent fiber melted whereas the polyester inner portion remained intact.

The above technique was found suitable to make molded structures, although the major component of the mixture is a thermoset foam. Molding became possible owing to the thermoplastic fibrous matrix. In certain cases, the ratio of fibers to foam has to be optimized to get a better molded part. In selecting the ratio, one should note that the hydrophilic foam contributes the absorbency and the resiliency, whereas the fibers are hydrophobic but impart dry and wet strength to the composite. The usable ratios, by weight, of foam to fiber can vary between about 80 foam:20 fiber and 40 foam:60 fiber, while the preferred ratios are from 70 foam:30 fiber to 50 foam:50 fiber.

The number of the components in the foam-fiber blend is not limited to two, but the blend must contain a resilient foam and a binder fiber. In addition, many other materials can be included depending on the desired properties of the final composite. Thus, wood pulp and other hydrophilic fibrous materials can be mixed in thereby to increase the wicking rate and to reduce the cost (as in Example III). They can be present in percentages, by weight, of the foam-fiber composite from 0–60%, with 10–50% being the preferred range, and 40% the most preferred amount, when such materials are used. Naturally the specific end-use purpose will influence the amounts used.

In carrying out the process of the present invention a carding machine may be used. Many different carding machines are available which are useful in the laboratory or on a commerical scale, for example, from Davis Feber, Hergeth Hollingsworth GmbH, John D. Hollingsworth on Wheels, Inc. and Asselin.

In carrying out the thermal bonding, typical laboratory oven-type equipment available includes Honeycomb Systems Inc. Thermal Bonder, and forced draft hot air oven from Fisher Co. and many other sources, while typical commercial equipment available includes AER Corporation's through-air bonders. Any forced air type oven may be used.

The preferred amino-ether foams are those described in U.S. Pat. No. 4,554,297. Other hydrophilic foams which may be used include polyurethane, Plastisol (PVC) and SBR (styrene butadiene rubber) treated with surfactant.

Where the amino-ether foam contains a super absorbent, super absorbents of the grafted starch type or of the polyacrylate type may be used such as are commercially available as Drytech (Dow Chemical), A-720 (Arakawa) and IM-1000 (Sanyo).

The superabsorbent can be incorporated in the foam by the following procedure: the superabsorbent powder is slurried in epoxy resin (Epon 828, Shell Chemical) heated to 100° C. (20 g powder in 50 g resin) and 5 g sodium bicarbonate is added. Jeffamine ED-600 (amine-terminated polyoxyethylene) (Texaco Chemical) 60 g is mixed with 4 g lactic acid and 2 g water. The two components are mixed thoroughly for 15 seconds and poured into a mold in a 130° C. oven. After 15 minutes, foam containing superabsorbent is obtained.

Where it is desired to incorporate in the composite, hydrophilic fluid-wickable fibrous materials, materials such as rayon, wood pulp, and acrylic are useful.

The most preferred thermoplastic fibers are a bicomponent (polyethylene/polyester) fiber available from Enka as Enka Fusible Fiber and also polyester bicomponent fibers. The polyethylene outer sheath portion of the bicomponent fiber will melt under the heating conditions used while the inner polyester remains intact. Instead of the two fiber materials being part of a bicomponent fiber, they may be separately used, individually, but together in combination. It is not necessary that polyethylene and polyester be selected the particular fibers to be used. Any thermoplastic fiber which will melt and fuse to the foam to form a matrix can be used in place of polyethylene. Typical other fusible thermoplastic polymer fibers of this type include: Chisso polyethylene/polypropylene, polyester bicomponent fibers, and Heterofil (ICI). Also, in place of the polyester, other relatively high melting fibers can be used such as: polamide (ICI).

The following examples are intended to illustrate, but not limit, the present invention. In all examples, the foam referred to is that of U.S. Pat. No. 4,554,247.

EXAMPLE 1

A 3 mm (⅛") thick sheet of polyaminoether foam was sandwiched between Enka bicomponent fibers. The proportion of foam to fiber by weight was 70:30 respectively. The sandwiched fiber-foam composite was passed through laboratory-size roller top carding equipment made by Davis Feber. The carding equipment opened the fibers, chopped the foam into small pieces about 3 mm (⅛") in size, and dispersed the chopped foam uniformly into the fibrous web. The carded foam/fiber composite was thermally bonded at 140° C. for about 5 minutes in an air circulating laboratory oven. The resulting composite structure was soft, resilient and absorbent. The density of the composite structure was 0.048 gm/cc (3 pounds per cubic foot), whereas the density of the starting foam was 0.06 gm/cc (3.8 pounds per cubic foot). Absorption capacity was 18 g water per gram of composite by the following procedure: a piece of the composite, about 1 gram, is accurately weighed, dipped in water, and the excess water is allowed to drain off. The wet sample is then reweighed to thereby calculate the amount of water each gram of composite holds.

EXAMPLE 2

Polyaminoether foam containing 15% water insoluble swellable material (superabsorbent) was first prepared in the manner previously described above for how to incorporate superabsorbent into foam. The foam was then sliced to about 3 mm (⅛") thick sheets and a resilient fiber, foam and superabsorbent composite structure was made as described in Example 1. The fluid retention under pressure of this composite was significantly higher than that of Example 1, being well over double.

EXAMPLE 3

A loose fibrous web of Enka bicomponent fiber and wood pulp fibers was prepared using Rando-Webber air-laid equipment. The 3 mm thick amino-ether foam sheet and fluffed wood pulp web were plied together to form the composite structure. This composite structure was sandwiched between the two layers of Enka fiber web. The composition of sandwiched structure was 15% wood pulp, 30% Enka fibers and 55% foam. The sandwiched structure was fed into the lickerin section of the air-laid web making equipment. The main lickerin cylinder of the equipment chopped the foam into small pieces about 3 mm (⅛") in size and blended fibers of various layers along with the foam pieces. The blended fiber/foam material was consolidated into a heterogeneous web. The web was thermally bonded in a laboratory oven at 140° C. The resultant bonded fiber/foam composite was soft, resilient and absorbent.

EXAMPLE 4

A block of amino-ether foam was first broken into chunks and then chopped into particles about 7 mm (¼") in size using a foam chopper made by Ormont Corporation (Imperial Fluffer and Picker) mill. The chopped foam was uniformly mixed with polyester/polyester sheath-core type bicomponent fiber in the ratio of 70:30 by weight foam/fiber. The mixing of foam and fibers was conducted by using a CMC (Carolina Machinery Company) Even Feed type of prefeeder to produce a uniform foam/fiber mat, which was fed into the carding equipment. The carding equipment opens the fibers, disperses foam into the fiber matrix, and produces uniform weight web. The web was thermally bonded in a laboratory oven at 120° C. The resultant foam/fiber composite was resilient and absorbent.

EXAMPLE 5

A low density composite consisting of 15% Hollow Core (Hollofil) polyester, 15% PE/PET bicomponent fiber and 70% foam was produced by following the procedure described in Example 4.

The use of Hollow Core polyester fiber, besides providing structural reinforcement to composite, provides high loftiness (bulk) to the composite. High bulk material which is low in density, provides large void volume which is essential for high absorbency composites.

EXAMPLE 6

(This is a comparative example using one single-component fiber.)

Seventy percent (70%) chopped foam and 30% low melting monocomponent polyester fiber (D-581, DuPont) were blended and web was produced in accordance with Example 4. The web was thermally bonded at 130° C. in a hot air oven. The resulting composite was resilient, but it had a poor tensile strength property.

The poor tensile strength property of the composite of this comparative example is attributed to the fact that upon thermal bonding of the web, the polyester fibers lost their fibrous characteristics. It is the fibers in the composite which retain their fibrous characteristics which provide the necessary structural reinforcement which results in a good tensile property.

One of the ways here found for improving tensile properties when using monocomponent fibers, is to physically blend some high melting (greater than 130° C.) fibers with the low melting fibers. The low melting fibers are used to bond the materials together, whereas high melting fibers would provide reinforcement to the structure. This is illustrated in Example 7.

EXAMPLE 7

The procedure followed was the same as in Example 6 except the mixture consisted of 70% foam, 15% binder fiber (D-581, DuPont polyester fiber) and 15% polyethylene-terepthalate (PET) fibers (m.p.=240° C.).

Bonding in a 130° C. hot air oven created a strong bonded matrix of PET, in which foam particles were dispersed. The composite obtained was similar in properties to that of Example 4.

We claim:

1. A resilient absorbent foam-fiber composite comprising large particles of an amino-ether hydrophilic foam uniformly distributed in and heat bonded to a thermoplastic fibrous matrix.

2. The composite of claim 1 wherein the foam is present in an amount of 20–80% by weight of the composite and the thermoplastic fibrous matrix contains at least one binder fiber.

3. The composite of claim 2 wherein the foam particles have a particle size of about 3–8 millimeters.

4. The composite of claim 2 wherein the foam used is the reaction product of amine terminated poly(alkylene oxide) and epoxy resin.

5. The composite of claim 2 wherein the foam contains a superabsorbent.

6. The composite of claim 2 wherein the thermoplastic fibrous matrix is made from at least two different fibers, one of which is low melting and has at least partially melted, and the other of which is high melting and has not melted.

7. The composite of claim 6 wherein the thermoplastic fibrous matrix is made from a bicomponent fiber made of two different fibers, where the core is made of a high melting material and the sheath of a lower melting material.

8. The composite of claim 7 wherein the high melting material used is polyester and the lower melting material used is polyethylene.

9. The composite of claim 6 wherein at least some of the fiber is a hollow core fiber.

10. The composite of claim 2 wherein a hydrophilic fibrous material is optionally also present in an amount of 0–60% by weight.

11. The composite of claim 10 wherein the hydrophilic fibrous material is wood pulp.

12. The composite of claim 11 wherein the wood pulp is present in an amount of from 10–50% by weight.

13. The process of preparing a resilient, absorbent foam-fiber composite comprising an animo-ether hydrophilic foam uniformly distributed in and heated bonded to a thermoplastic fibrous matrix which comprises blending small pieces of amino-ether hydrophilic foam and of thermoplastic fiber so as to form a uniform web, heating said web to thermally bond the thermoplastic fiber to the foam thereby to form the composite.

14. The process of claim 13 wherein the foam and fiber are combined and chopped sumultaneously into large particles.

15. The process of claim 14 wherein the foam is preground before being combined with the fiber.

16. The process of claim 14 wherein the large particles are 3–8 millimeters.

17. The process of claim 13 wherein the foam used is the reaction product of amine terminated poly(alkylene oxide) and epoxy resin.

18. The process of claim 13 wherein the foam used contains a superabsorbent.

19. The process of claim 13 wherein the thermoplastic fiber used is made from at least two different fibers, one of which is low melting and can at least partially melt, and the other of which is high melting and cannot melt during the thermal bonding heating step.

20. The process of claim 19 wherein the thermoplastic fiber used is made from a bicomponent fiber made of two different fibers, where the core is made of a high melting material and the sheath of a lower melting material.

21. The process of claim 20 wherein the high melting material used is polyester and the lower melting material used is polyethylene.

22. The process of claim 19 wherein at least some of the fiber is a hollow core fiber.

23. The process of claim 13 wherein a hydrophilic fibrous material is optionally also present in an amount of 0-60% by weight.

24. The process of claim 23 wherein the hydrophilic fibrous material is wood pulp.

25. The process of claim 24 wherein the wood pulp is present in an amount of from 10-50% by weight.

* * * * *